US00PP35156P2

(12) United States Plant Patent
Mowrey et al.

(10) Patent No.: US PP35,156 P2
(45) Date of Patent: May 9, 2023

(54) BLUEBERRY PLANT NAMED 'DRISBLUETWENTYEIGHT'

(50) Latin Name: ***Vaccinium corymbosum* L.**
Varietal Denomination: DrisBlueTwentyEight

(71) Applicant: Driscoll's, Inc., Watsonville, CA (US)

(72) Inventors: Bruce D. Mowrey, Watsonville, CA (US); Jennifer K. Izzo, Watsonville, CA (US); Jaime Patzer, Watsonville, CA (US); Christian Christensen, Watsonville, CA (US); Stephanie Fong, Watsonville, CA (US); James Olmstead, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 17/961,286

(22) Filed: Oct. 6, 2022

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ... A01H 5/08; A01H 5/00; A01H 5/02; A01H 6/36; A01H 6/368
See application file for complete search history.

(56) References Cited

U.S. PATENT DOCUMENTS

PP6,699 P 3/1989 Wood
PP11,807 P2 3/2001 Lyrene
PP12,783 P2 7/2002 Lyrene
PP15,146 P3 9/2004 Hancock
PP19,503 P3 11/2008 Lyrene
PP20,436 P2 10/2009 Caster et al.
PP20,449 P2 11/2009 Caster et al.
PP20,488 P2 11/2009 Caster et al.
PP24,407 P3 4/2014 Caster et al.
PP24,489 P3 5/2014 Lyrene et al.
PP24,568 P3 6/2014 Caster et al.
PP24,569 P3 6/2014 Caster et al.
PP24,605 P3 7/2014 Caster et al.
PP26,287 P3 1/2016 Caster et al.
PP26,451 P3 3/2016 Rodriguez et al.
PP26,537 P3 3/2016 Caster et al.
PP26,643 P3 4/2016 Caster et al.
PP26,748 P3 5/2016 Rodriguez et al.
PP27,622 P3 1/2017 Caster et al.
PP28,933 P2 2/2018 Caster et al.
PP31,649 P2 * 4/2020 Caster ..... A01H 5/08 Plt./157
PP31,650 P2 4/2020 Caster et al.
PP31,685 P2 4/2020 Mowrey et al.
PP31,698 P2 4/2020 Mowrey et al.
PP32,267 P2 10/2020 Caster et al.
PP32,744 P3 1/2021 Caster et al.
PP32,876 P2 3/2021 Mowrey et al.
PP33,066 P2 5/2021 Mowrey et al.
PP33,718 P2 12/2021 Caster et al.
PP34,067 P2 3/2022 Caster et al.
PP34,179 P2 5/2022 Mowrey et al.
PP34,316 P2 6/2022 Mowrey et al.

* cited by examiner

*Primary Examiner* — June Hwu

(74) *Attorney, Agent, or Firm* — Morrison & Foerster LLP

(57) ABSTRACT

A new and distinct variety of blueberry plant named 'DrisBlueTwentyEight', particularly selected for the large size, sweet flavor, and heavy bloom layer of its fruit, is disclosed.

7 Drawing Sheets

Latin name:
Botanical classification: *Vaccinium corymbosum* L.
Varietal denomination: The varietal denomination of the claimed variety of blueberry plant is 'DrisBlueTwentyEight'.

BACKGROUND OF THE INVENTION

Blueberry plants are perennial flowering plants with indigo-colored berries from the section *Cyanococcus* within the genus *Vaccinium*. Many commercially sold species with English common names, including blueberry, are currently classified in section *Cyanococcus* of the genus *Vaccinium* and come predominantly from North America. Many North American native species of blueberries are grown commercially in the Southern Hemisphere in Australia, New Zealand, and South American nations.

*Vaccinium corymbosum*, the northern highbush blueberry, is a North American species of blueberry which has become a food crop of significant economic importance. It is native to eastern Canada and the eastern and southern United States, from Ontario east to Nova Scotia and south as far as Florida and eastern Texas. It has been naturalized in Europe, Japan, New Zealand, and the Pacific Northwest of North America. Other common names include blue huckleberry, tall huckleberry, swamp huckleberry, high blueberry, and swamp blueberry.

Blueberries are usually erect, prostrate shrubs that can vary in size from approximately four inches to approximately 13 feet in height. In the commercial production of blueberries, the smaller species are known as "lowbush blueberries", while the larger species are known as "highbush blueberries".

Blueberry bushes typically bear fruit in the middle of the growing season. However, fruiting times can be affected by local conditions such as altitude and latitude. As such, peak crop can vary from May to August in the northern hemisphere, depending upon these conditions.

Blueberries are a popular fruit that is typically consumed as fresh fruit, individually quick frozen (IQF) fruit, or in prepared foods, such as purées, juices, jellies, jams, baked goods, snack foods, and cereals.

Blueberry is an important and valuable fruit crop. Accordingly, there is a need for new varieties of blueberry plant. In particular, there is a need for improved varieties of blueberry plant that are stable, high yielding, and agronomically sound.

SUMMARY OF THE INVENTION

In order to meet these needs, the present invention is directed to an improved variety of blueberry plant. In particular, the invention relates to a new and distinct variety of blueberry plant (*Vaccinium corymbosum* L.), which has been denominated as 'DrisBlueTwentyEight'.

Blueberry plant variety 'DrisBlueTwentyEight' was selected in Santa Cruz County, Calif. in September of 2013 and originated from a controlled cross between the female parent blueberry plant 'DrisBlueTwentyFour' (U.S. Plant Pat. No. 34,067) and the proprietary male parent blueberry plant '52E 3' (unpatented). The original seedling of the new variety was first asexually propagated via softwood cuttings and tissue culture in Santa Cruz County, Calif. in September of 2013.

'DrisBlueTwentyEight' was subsequently asexually propagated via softwood cuttings and tissue culture and underwent further testing in Linn County, Oreg. for two years (2019 to 2021). The present blueberry variety has been found to be stable and reproduce true to type through successive asexual propagations via softwood cuttings and tissue culture.

'DrisBlueTwentyEight' was selected for the large size, sweet flavor, and heavy bloom layer of its fruit.

BRIEF DESCRIPTION OF THE DRAWINGS

This new blueberry plant variety is illustrated by the accompanying photographs. The colors shown are as true as can be reasonably obtained by conventional photographic procedures. The photographs are of plants that are five years old, unless otherwise specified.

DETAILED BOTANICAL DESCRIPTION

Figure 1:
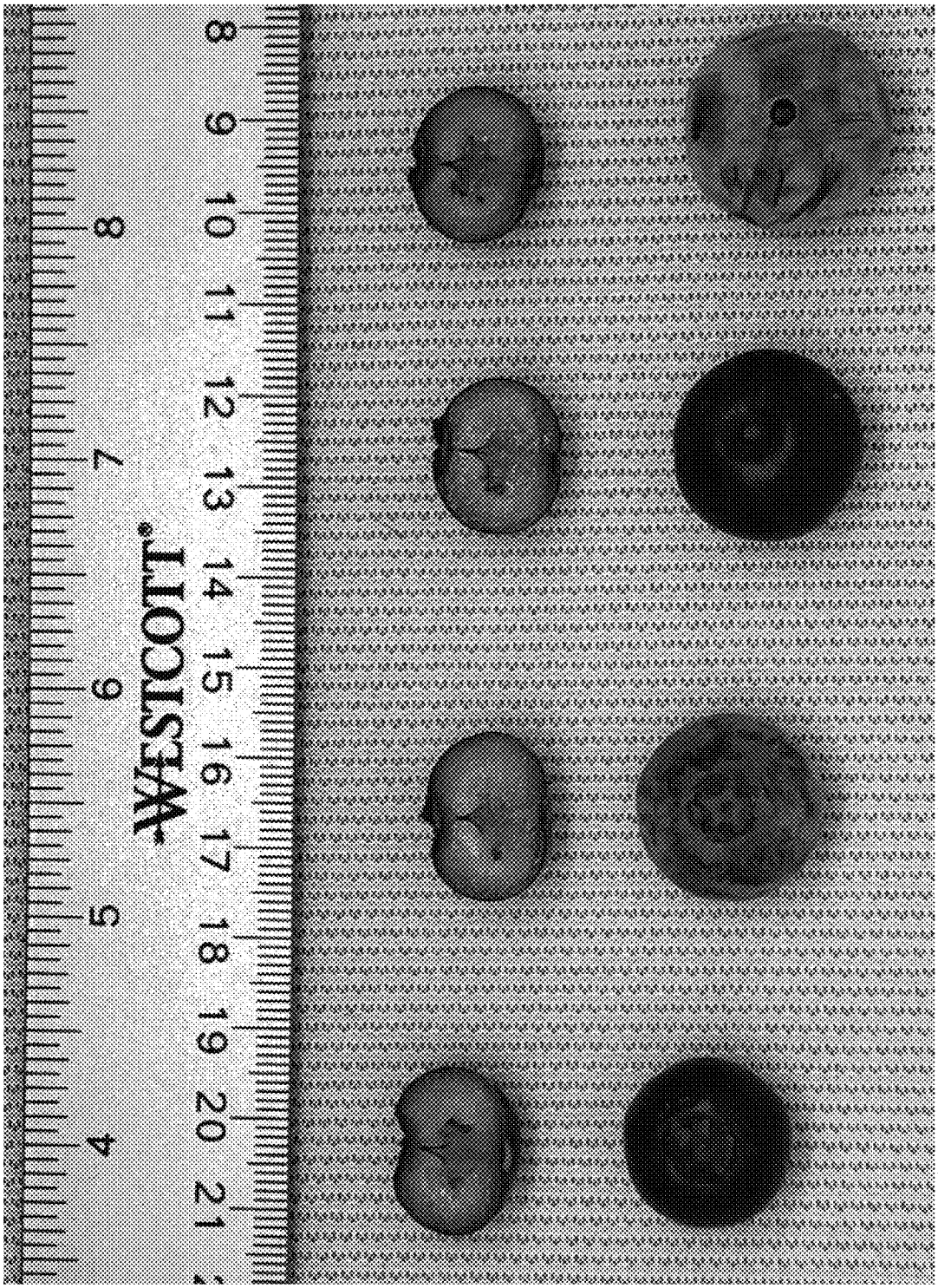
FIG. 1 illustrates longitudinal sections (top row) and whole fruit (bottom row; calyx side up on left, pedicel side up on right) of variety 'DrisBlueTwentyEight'. The second and fourth fruit of the bottom row have bloom on them, whereas the first and third fruit of the bottom row have bloom removed.
Figure 2:
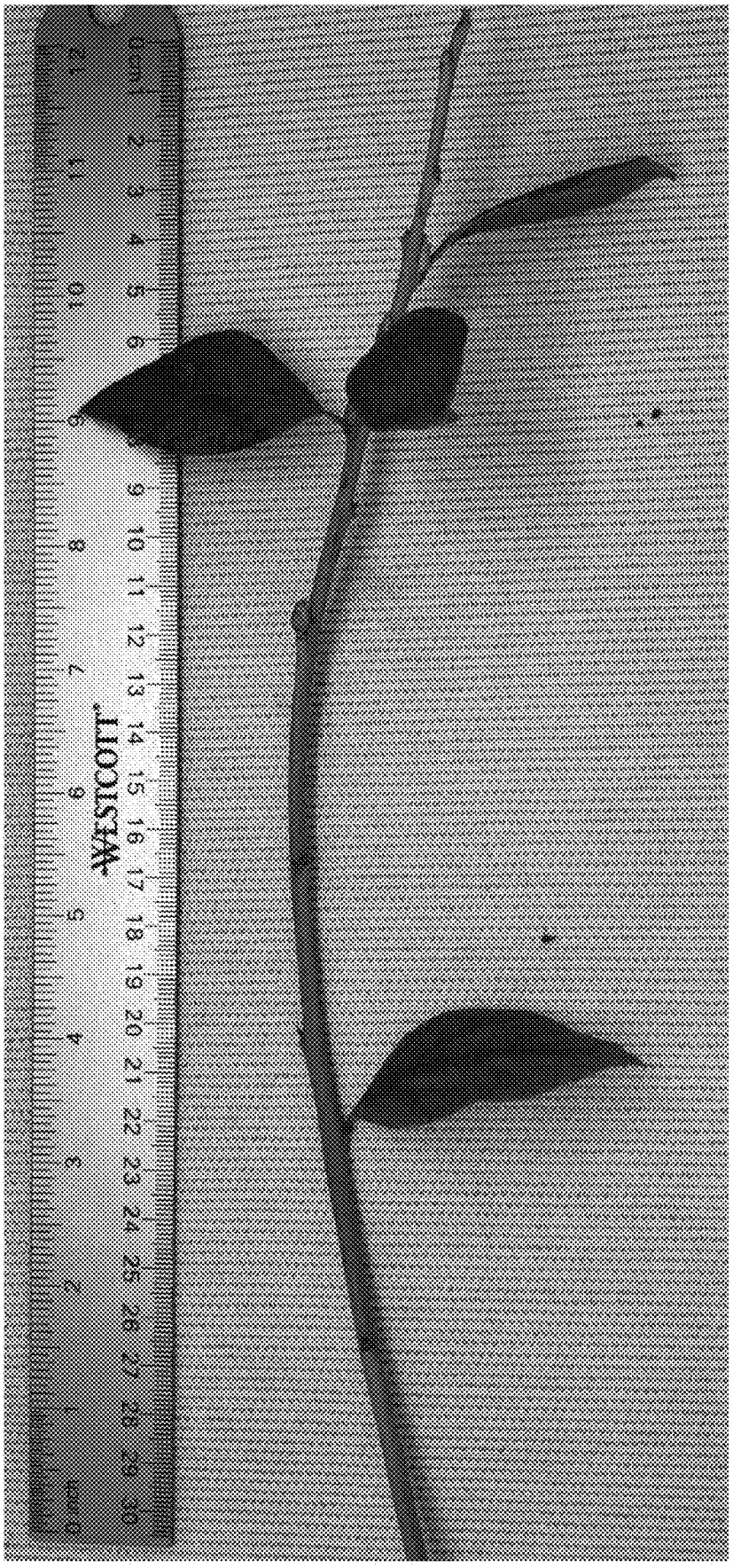
FIG. 2 illustrates a section of a cane of variety 'DrisBlueTwentyEight'.
Figure 3:
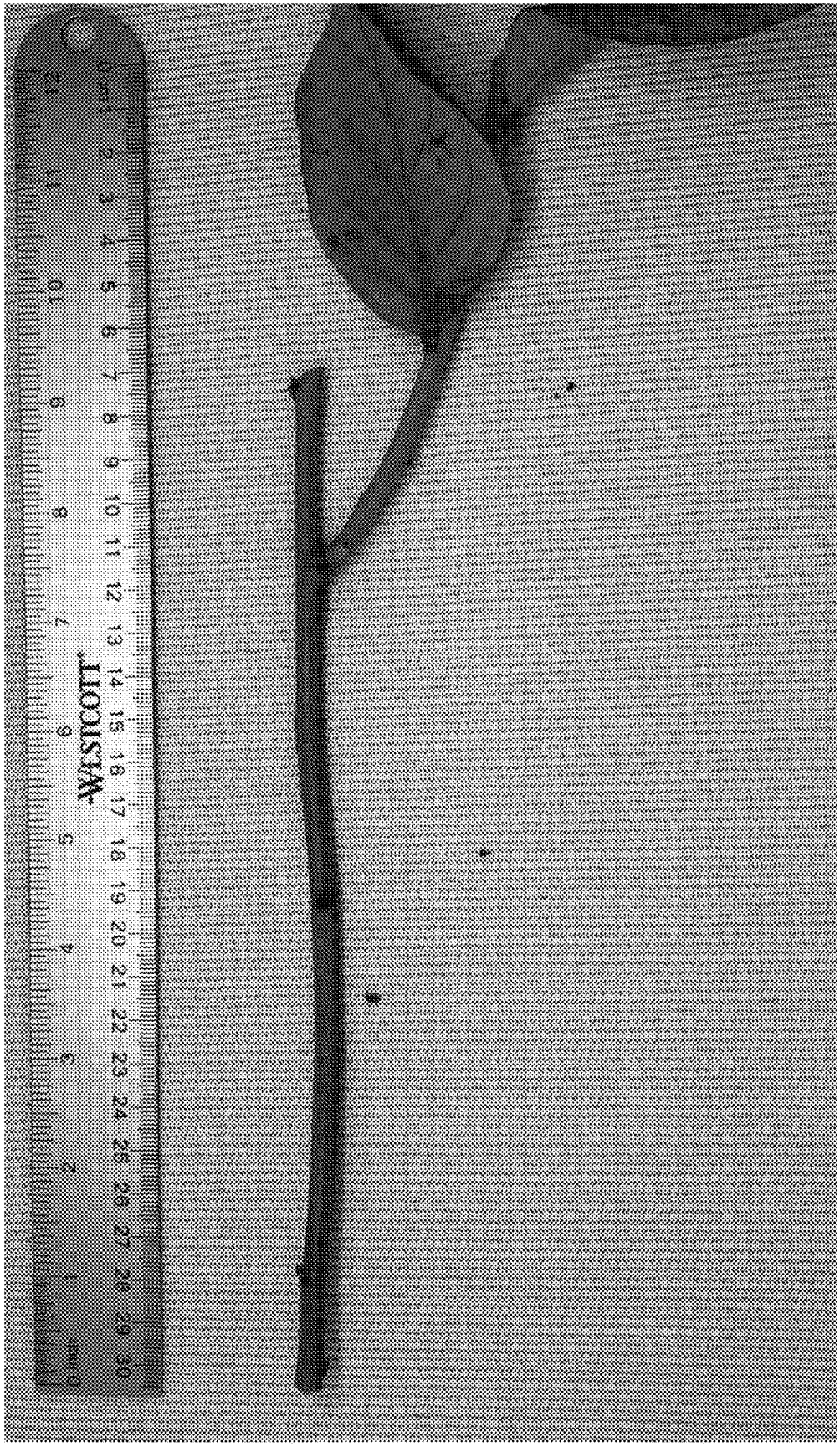
FIG. 3 illustrates another view of a section of a cane of variety 'DrisBlueTwentyEight'.
Figure 4:
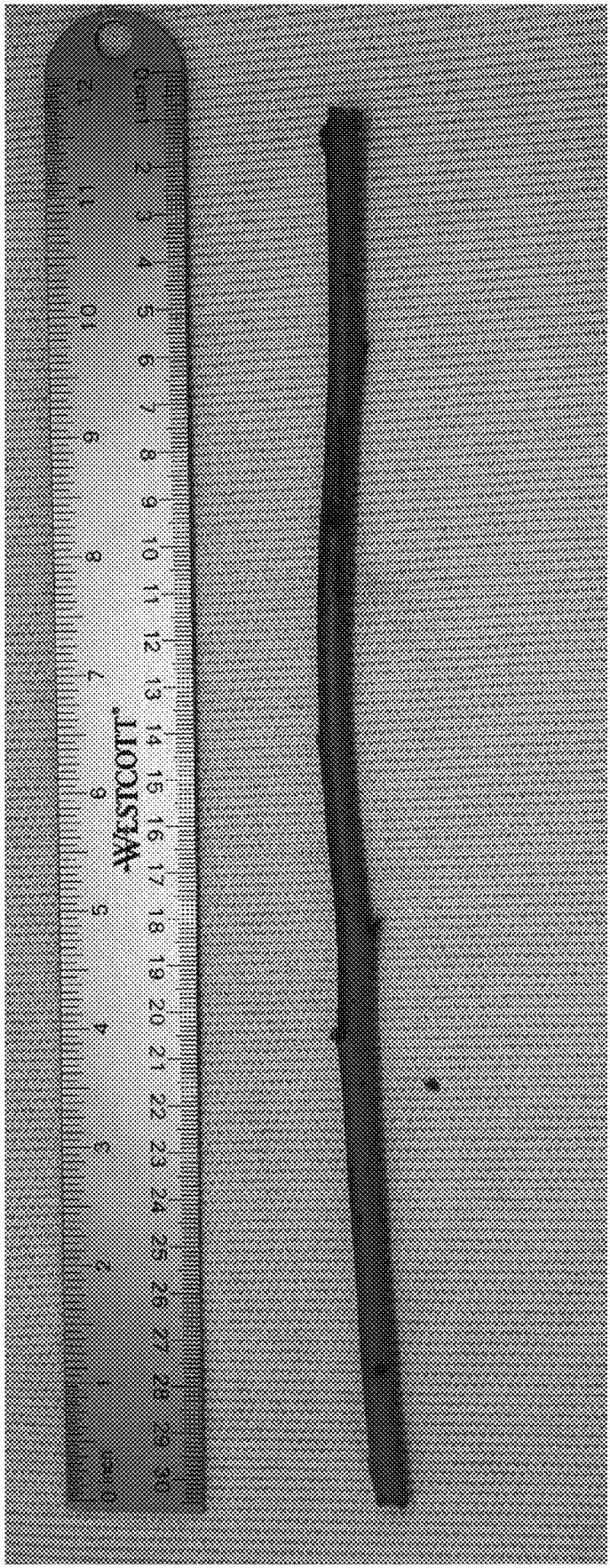
FIG. 4 illustrates another view of a section of a cane of variety 'DrisBlueTwentyEight'.
Figure 5:
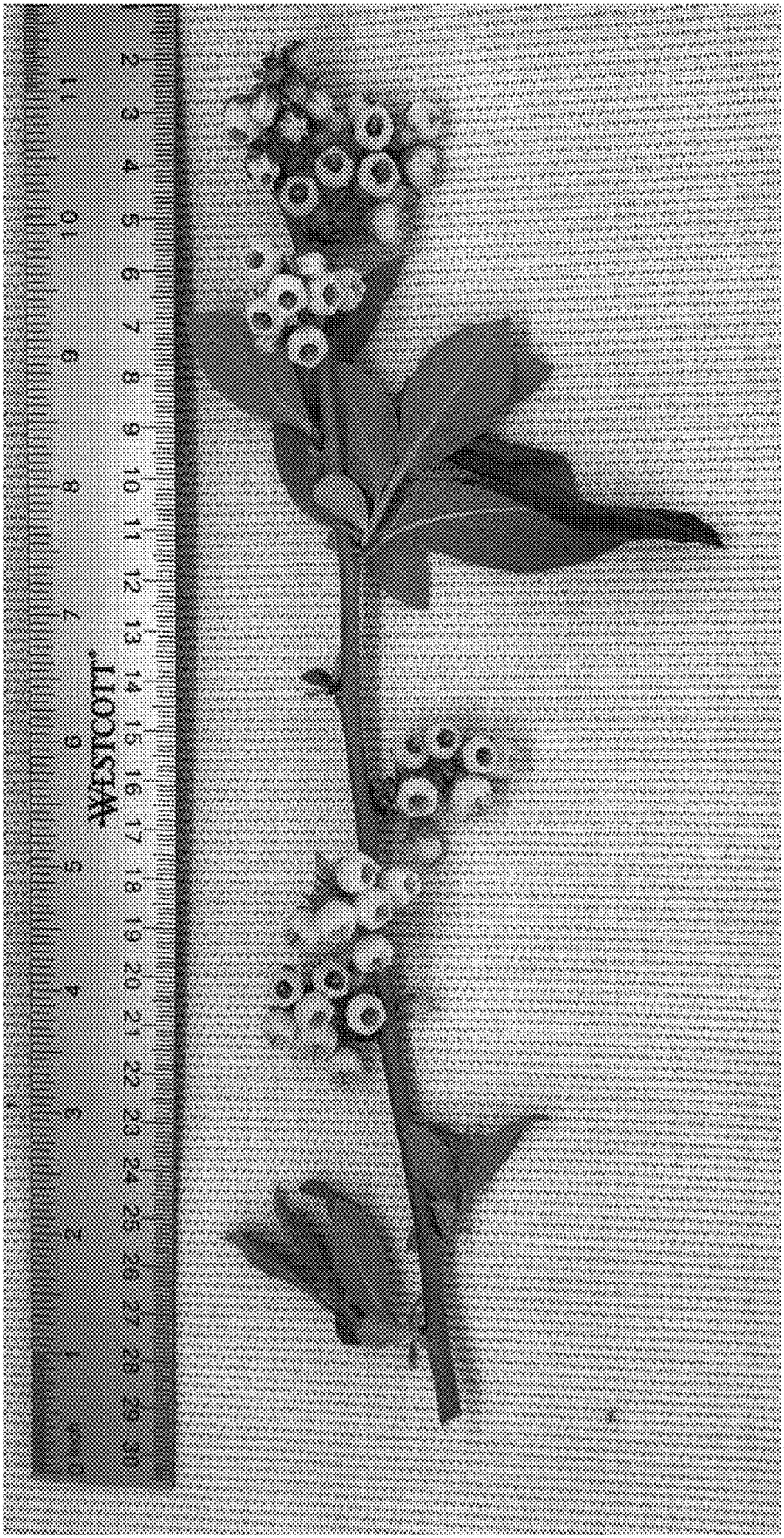
FIG. 5 illustrates clusters of flowers of variety 'DrisBlueTwentyEight'.
Figure 6:
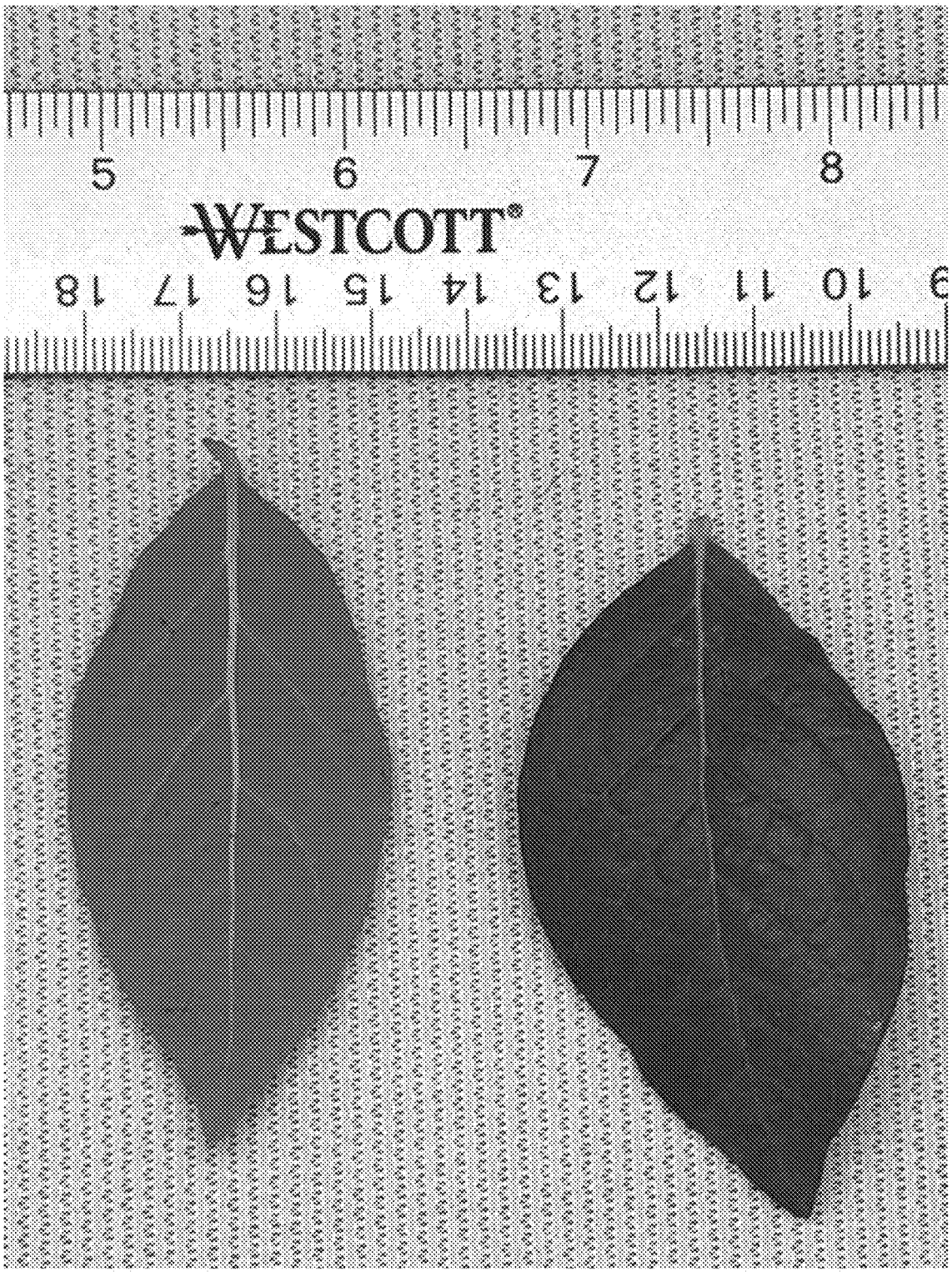
FIG. 6 illustrates the lower surface (left) and upper surface (right) of leaves of variety 'DrisBlueTwentyEight'.
Figure 7:
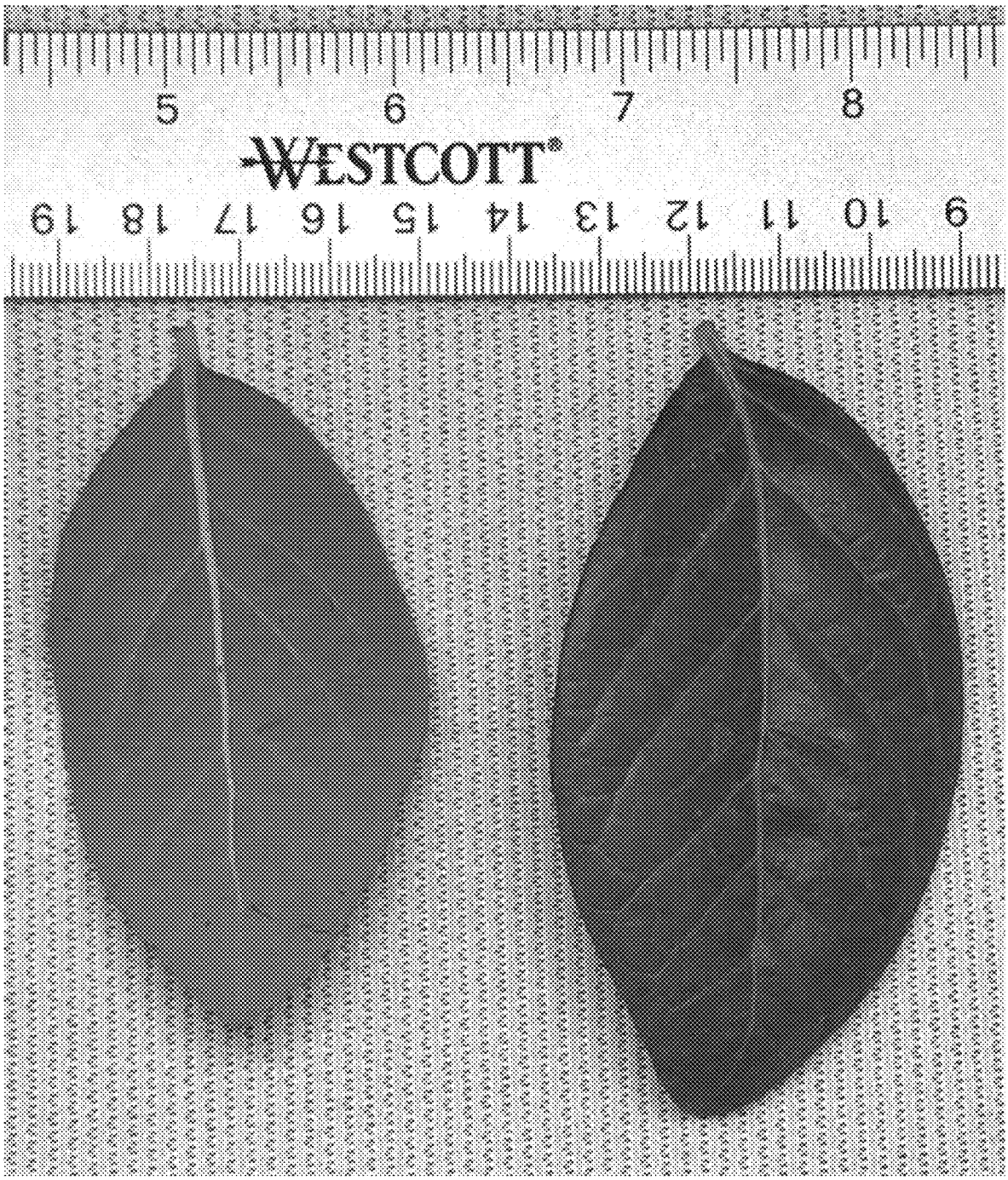
FIG. 7 illustrates another view of the lower surface (left) and upper surface (right) of leaves of variety 'DrisBlueTwentyEight'.

The following description sets forth the distinctive characteristics of 'DrisBlueTwentyEight'. The data which define these characteristics is based on observations taken in Linn County, Oreg. from 2019 to 2021. This description is in accordance with UPOV terminology. Color designations, color descriptions, and other phenotypical descriptions may deviate from the stated values and descriptions depending upon variation in environmental, seasonal, climatic and cultural conditions. 'DrisBlueTwentyEight' has not been observed under all possible environmental conditions. Unless noted otherwise, the botanical description of 'DrisBlueTwentyEight' was taken from plants that were five years old. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* 2$^{nd}$ edition by James G. Harris and Melinda Woolf Harris, unless where otherwise defined.

Classification:

*Family*.—Ericaceae.

*Botanical*.—*Vaccinium corymbosum* L.

*Common name*.—Blueberry.

*Variety name*.—'DrisBlueTwentyEight'.

Parentage:

*Female parent*.—'DrisBlueTwentyFour' (U.S. Plant Pat. No. 34,067).

*Male parent*.—Proprietary blueberry plant '52E 3' (unpatented).

Plant:

*Height*.—133.22 cm.

*Width*.—151.38 cm.

*Length width ratio*.—0.9.

*Vigor*.—Medium.

*Growth habit*.—Semi-upright.

*Cane renewal*.—Weak.

*Chilling requirements*.—'DrisBlueTwentyEight' is a mid-chill variety and has been grown in regions with chill hour accumulation between 500 to 1000 hours below 7° C., as well as producing high yield when grown in areas with at least 500 chill hours below 7° C. Early bloom may occur in areas where the chill requirement is met before the last potential freeze.

*Time of vegetative bud burst*.—Mid- to late February.

*One-year-old shoot* (*young canes*).—Length: 22.80 cm. Diameter at the base: 3.66 mm. Diameter at the tip: 2.04 mm. Internode length on the upper half: 20.76 mm. Color: RHS 151A (Strong greenish yellow). Texture: Smooth.

*Five-year-old shoot* (*mature canes*).—Length: 72.77 cm. Diameter at the base: 29.02 mm. Diameter at the tip: 10.56 mm. Internode length on the upper half: 64.49 mm. Color: RHS 199D (Dark greyish yellow). Texture: Rough.

Leaves:

*Length*.—6.80 cm.

*Width*.—3.88 cm.

*Length/width ratio*.—1.8.

*Shape*.—Elliptic.

*Margin*.—Entire.
*Apex shape*.—Acute.
*Base shape*.—Cuneate.
*Arrangement*.—Alternate.
*Venation*.—Reticulate.
*Vein color*.—RHS 154D (Light yellow green).
*Color on upper side*.—RHS 146A (Moderate olive green).
*Color on lower side*.—RHS 147C (Moderate yellow green).
*Glaucosity on upper side*.—Medium.
*Trichomes on upper side*.—Glabrous (absent).
*Glossiness*.—Glossy.
*Petiole*.—Length: 3.92 mm. Diameter: 1.95 mm. Color: RHS N144D (Strong yellow green).

Flowers:
*Flower length* (*excluding pedicel*).—11.00 mm.
*Flower width*.—6.54 mm.
*Flower length/width ratio*.—1.7.
*Fragrance*.—Faint.
*Inflorescence peduncle*.—Length: 14.48 mm. Diameter: 1.39 mm. Color: RHS N57B (Vivid purplish red).
*Flower bud*.—Length of dormant bud: 5.46 mm. Width of dormant bud: 2.52 mm. Number of flowers per bud: 7.30. Anthocyanin coloration at bud break: Medium. Anthocyanin color: RHS 67D (Strong purplish pink).
*Flower pedicel*.—Length: 5.65 mm. Diameter: 1.03 mm. Color: RHS 143C (Strong yellow green).
*Corolla*.—Shape: Globose. Color of corolla tube at open flower stage: RHS 4D (Pale yellow green). Anthocyanin coloration of corolla tube on outer side (late pink bud stage): Weak. Anthocyanin color: RHS 69A (Very pale purple). Conspicuousness of ridges on corolla tube: Medium. Color of receptacle: RHS 143A (Strong yellow green). Diameter of corolla aperture: 3.51 mm. Petal: Petal width (ridge to ridge): 2.11 mm. Sepal: Length: 3.41 mm. Width: 3.26 mm. Color: RHS 124B (Light bluish green).
*Reproductive organs*.—Style: Length (including stigma): 8.96 mm. Color: RHS 144C (Strong yellow green). Ovary: Color: RHS 146A (Moderate olive green). Stamen: Length: 6.46 mm. Color: RHS 26A (Strong orange). Pollen: Amount: High. Pollen color: RHS 4D (Pale yellow green).
*Flowering interval on one-year-old shoot*.—Late March through mid-May.

Fruit:
*Length*.—14.88 mm.
*Width*.—19.67 mm.
*Length/width ratio*.—0.8.
*Weight*.—2.40 grams/fruit.
*Shape in longitudinal section*.—Oblate.
*Attitude of sepals*.—Incurved.
*Calyx basin*.—Diameter: 6.93 mm. Depth: 2.13 mm. Diameter/depth ratio: 3.3.
*Infructescence* (*fruit cluster*).—Number of berries per cluster: 7.00. Density: Medium. Peduncle length: 19.27 mm. Peduncle diameter: 1.81 mm.
*Fruit pedicel*.—Length: 8.20 mm. Diameter: 1.23 mm.
*Color of unripe fruit*.—RHS 192C (Very pale green).
*Intensity of bloom*.—Strong.
*Color of skin with bloom on mature fruit*.—RHS 106D (Very pale purplish blue).
*Color of skin after removal of bloom on mature fruit*.—RHS N186A (Dark purplish grey).
*Flesh color*.—RHS 145D (Light yellow green).
*Fruit firmness*.—Firm.
*Sweetness/soluble solids* (*in ° brix*).—16.50.
*Titratable acidity* (*% as citric acid*).—0.49%.
*Seed*.—Diameter: 0.91 mm. Color: RHS 164A (Brownish orange). Abundance: High.
*Fruiting*.—Fruiting type: On one-year-old shoots only. Harvest interval on one-year-old shoot: Mid-July through mid-August. Yield: 3.5 kg to 4.5 kg of fruit per plant per season from 50-month old plants when grown at Linn County, Oreg.

Resistance to abiotic stress, pests, and diseases:
*Heat*.—Moderately susceptible.
*Botrytis fruit rot* (*botrytis cinerea*).—Susceptible.
*Blueberry shock virus*.—Highly susceptible.
*Pseudomonas* (*pseudomonas syringae*): Moderately resistant.
*Phomopsis* (*phomopsis vaccinii*): Highly susceptible.

COMPARISONS TO PARENTAL AND REFERENCE BLUEBERRY VARIETIES

'DrisBlueTwentyEight' differs from the female parent and reference variety 'DrisBlueTwentyFour' (U.S. Plant Pat. No. 34,067) in that 'DrisBlueTwentyEight' has firm fruit, early time of beginning of vegetative growth, medium infructescence density, and strong intensity of bloom on fruit, whereas 'DrisBlueTwentyFour' has medium firm fruit, medium time of beginning of vegetative growth, sparse infructescence density, and medium intensity of bloom on fruit.

'DrisBlueTwentyEight' differs from the male parent proprietary blueberry plant '52E 3' (unpatented) in that 'DrisBlueTwentyEight' has earlier production, higher yield potential, and larger fruit size compared to '52E 3'.

'DrisBlueTwentyEight' differs from the reference blueberry plant variety 'DrisBlueEighteen' (U.S. Plant Pat. No. 31,649) in that 'DrisBlueTwentyEight' has early time of beginning of vegetative growth, elliptic leaf shape, medium flower bud anthocyanin coloration, and globose shape of corolla, whereas 'DrisBlueEighteen' has medium time of beginning of vegetative growth, lanceolate leaf shape, strong flower bud anthocyanin coloration, and urceolate shape of corolla.

What is claimed is:

1. A new and distinct variety of blueberry plant designated 'DrisBlueTwentyEight' as shown and described herein.

* * * * *